United States Patent [19]

Karadavidoff et al.

[11] 4,139,631
[45] Feb. 13, 1979

[54] ESTERS OF DISUBSTITUTED ISOBUTYRIC ACIDS AND PHARMACEUTICAL COMPOSITIONS CONTAINING THE SAME

[75] Inventors: Isaac Karadavidoff, Paris; Milorad Stjepanovic, Chatou; Michele Moreau; Philippe Rohrbach, both of Paris, all of France

[73] Assignee: Bottu, Nanterre, France

[21] Appl. No.: 850,844

[22] Filed: Nov. 11, 1977

[30] Foreign Application Priority Data

Nov. 18, 1976 [FR] France .................................. 76 34702

[51] Int. Cl.$^2$ ..................... A61K 31/34; C07D 307/16
[52] U.S. Cl. .................................. 424/285; 260/347.4; 260/347.5; 424/248.55; 424/250; 544/152; 544/379
[58] Field of Search .......................... 260/347.4, 347.5; 424/285

[56] References Cited

U.S. PATENT DOCUMENTS 3,334,096   8/1967   Szarvasi et al. ................ 260/347.4 X
3,872,112   3/1975   Szarvasi ............................ 260/347.5

FOREIGN PATENT DOCUMENTS

M3843   1/1966   France.

OTHER PUBLICATIONS

Moffett et al., J. Am. Pharm. Assoc. Ed. Sci., vol. 42 (1953) pp. 717–719.

Primary Examiner—Richard Raymond
Attorney, Agent, or Firm—Poms, Smith, Lande & Glenny

[57] ABSTRACT

Pharmacologically valuable esters of isobutyric acid have the general formula

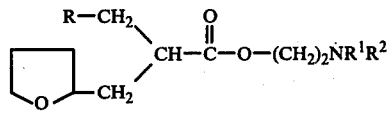

in which R is biphenylyl, norbornyl or para-cyclohexylphenyl and $R^1$ and $R^2$ are each lower alkyl groups or $R^1$ and $R^2$ together with the nitrogen atom to which they are linked is a saturated heterocyclic group which may contain an additional hetero atom. The esters may be used in the form of their salts with pharmaceutically acceptable acids.

The esters and their salts possess spasmolytic and vasodilatory activity and are useful in the treatment of arterial disorders.

9 Claims, No Drawings

ESTERS OF DISUBSTITUTED ISOBUTYRIC ACIDS AND PHARMACEUTICAL COMPOSITIONS CONTAINING THE SAME

The present invention relates to novel esters of disubstituted isobutyric acid, to a method of preparing the same and to pharmaceutical compositions containing the same.

The esters of the present invention are represented by the general formula

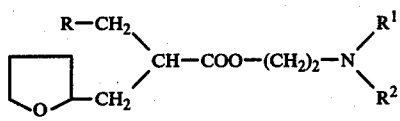

in which R is a biphenylyl, norbornyl or p-cyclohexylphenyl group, and $R^1$ and $R^2$ are each lower alkyl groups or, $R^1$ and $R^2$ taken together with the nitrogen atom to which they are linked, may form a saturated heterocyclic nucleus which may contain an additional heteroatom. The saturated heterocyclic nucleus may be a morpholinyl or piperazyl group.

The invention also includes the addition salts which the esters having the general formula (I) form with pharmaceutically acceptable mineral and organic acids such as oxalic acid, fumaric acid and citric acid.

The esters of the present invention are obtained by esterifying the corresponding monocarboxylic acids having the general formula:

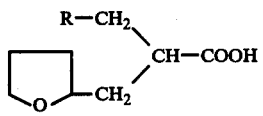

in which R is as defined above, by reaction with halides having the general formula:

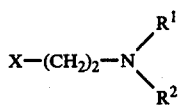

in which $R^1$ and $R^2$ are as defined above. Suitable halides for use in this process are dimethylaminoethyl bromide, diethylaminoethyl chloride and bromide, N-(2-bromoethyl)-piperazine, and N-(2-chloroethyl) and N-(2-bromoethyl)-morpholine.

The acids having the general formula (II) are prepared by hydrolysing, with potash in the presence of an alcohol, α,α-disubstituted diethyl malonates having the general formula:

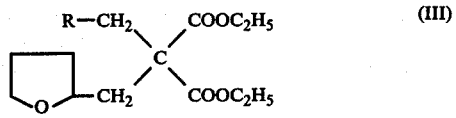

in which R is as defined above. The potassium salts thus produced are acidified with an aqueous strong acid and the free acids thus liberated are isolated and then decarboxylated.

The α,α-disubstituted ethyl malonates having the general formula (III) are preferably obtained from diethyl α-tetrahydrofurfuryl malonate having the formula:

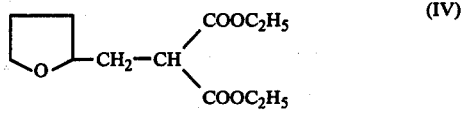

by reaction with a sodium alcoholate followed by condensation of the resulting sodium derivative with a halide having the general formula $R - CH_2 - X$ in which X is a chlorine or bromine atom and R is as defined above.

The esters of the present invention are isolated either in the pure state or, more preferably, in the form of the salts which they form with pharmaceutically acceptable acids such as fumaric acid, oxalic acid and citric acid.

The esters of the invention possess interesting pharmacological properties. When tested on animals, they have been shown to possess spasmolytic and vasodilatory properties, which makes them of interest from the therapeutic point of view for the treatment of circulatory disorders associated with arterial disease, hypertension and vascular aging.

The product may be administered either directly by intravenous or intramuscular injection (for example, as a 1% aqueous solution), or by perfusion (diluted with an isotonic solution), or by the oral route, in doses of 100 to 500 mg per day. For the oral route, tablets or capsules containing the active ingredient together with one or more solid diluents are most conveniently utilised.

The following examples illustrate the preparation of the esters according to the invention.

(A) SYNTHESIS OF α,α-DISUBSTITUTED ETHYL MALONATES (1) Diethyl α-tetrahydrofurfuryl-α-(4-biphenylmethyl) malonate Sodium ethylate is prepared by placing 2.07 g of sodium and 80 ml of ethanol in a flask. 21.9 g of ethyl tetrahydrofurfuryl malonate is then added and the mixture refluxed for 3 hours. After cooling to 50° C., 20 g of 4-chloromethyl-para-biphenyl is added. After refluxing for 15 hours, the mixture is poured into 250 ml of iced water and the product extracted with diethyl ether. A liquid is obtained having a boiling point of 226°–229° C. at a pressure of 0.5 mm of mercury.

(2) Diethyl α-tetrahydrofurfuryl-α-(3-biphenylmethyl) malonate

By proceeding in the same way as described in paragraph (1), using 9.4 g of 3-chloromethylbiphenyl instead of 4-chloromethyl-para-biphenyl, 11.9 g of a product is obtained (yield 69%) having a boiling point of 215°–220° C. at a pressure of 0.5 mm of mercury.

(3) Diethyl α-tetrahydrofurfuryl-α-(2-biphenylylmethyl) malonate

By proceeding in exactly the same way as described in paragraph (1), using 23.9 g of 2-chloromethylbiphenyl instead of 4-chloromethyl-para-biphenyl, 30.4 g of a product is obtained which has a boiling point of 207°–209° C. at a pressure of 0.3 mm of mercury.

(4) Diethyl α-tetrahydrofurfuryl-α-norbornylmethyl malonate

By proceeding in exactly the same way as described in paragraph (1), using 2-bromomethylnorbornane in place of the 4-chloromethyl-para-biphenyl and refluxing for 30 hours, a product is obtained which has a boiling point of 165°–168° C. at a pressure of 0.7 mm of mercury.

(5) Diethyl α-tetrahydrofurfuryl-α-(p-cyclohexylphenylmethyl) malonate

By proceeding exactly as described in paragraph (1), using 1-chloromethyl-4-cyclohexylbenzene in place of the 4-chloromethyl-para-biphenyl, a product is obtained which has a boiling point of 200°–205° C. at a pressure of 0.3 mm of mercury.

(B) SYNTHESIS OF THE DISUBSTITUTED ACIDS OF GENERAL FORMULA II

(1) β-Tetrahydrofuryl-β'-(4-biphenylyl)isobutyric acid

A mixture of 24.1 g of the diethyl malonate prepared as above (see paragraph A-1), 11 g of potash in 30 ml of water, and 60 ml of ethanol is refluxed for 10 hours. The mixture is then diluted with water and washed with ether. The aqueous solution is made acid by adding concentrated hydrochloric acid. The acid is extracted with diethyl ether. The residue after evaporating to dryness under reduced pressure is heated under nitrogen at 180°–200° C. for 2.5 hours. The product crystallises after cooling a solution thereof in light petroleum. The crystals are dried and washed with diisopropyl ether. The melting point of the product so obtained is 108°–109° C.

(2) β-Tetrahydrofuryl-β'-(3-biphenylyl)isobutyric acid

By proceeding in the same way as described in paragraph (1) above and using diethyl α-tetrahydrofurfuryl-α-(3-biphenylylmethyl) malonate as starting material, the desired product is obtained in the form of a very viscous yellow oil.

(3) β-Tetrahydrofuryl-β'-(2-biphenylyl)isobutyric acid

By proceeding in the same way as described in paragraph (1) and using diethyl α-tetrahydrofurfuryl-α-(2-biphenylylmethyl) malonate as starting material, the desired product is obtained in the form of an oil having a boiling point of 208°–211° C. at a pressure of 0.4 mm of mercury.

(4) β-Tetrahydrofuryl-β'-norbornyl isobutyric acid

By proceeding in the same way as described in paragraph (1) and using diethyl α-tetrahydrofurfuryl-α-norbornylmethyl malonate as starting material, the desired product is obtained in the form of an oil having a boiling point of 161°–166° C. at a pressure of 0.05 mm of mercury.

(5) β-Tetrahydrofuryl-β'-(p-cyclohexylphenyl) isobutyric acid

By proceeding in the same way as described in paragraph (1) and using diethyl α-tetrahydrofurfuryl-α-(p-cyclohexylphenylmethyl) malonate as starting material, the desired product is obtained in the form of an oil having a boiling point of 210°–215° C. at a pressure of 0.4 mm of mercury.

(C) SYNTHESIS OF THE OXALATES OF THE DIETHYLAMINOETHYL ESTERS OF THE ACIDS PREPARED AS DESCRIBED UNDER (B)

(1) The acid oxalate of the diethylaminoethyl ester of β-tetrahydrofuryl-β'-(4-biphenylyl) isobutyric acid A mixture of 8 g of the acid prepared as described in paragraph B-1, in 3.5 g of 2-chloroethyldiethylamine and 40 ml of isopropanol is refluxed for 8 hours. After evaporating the isopropanol to dryness under reduced pressure, the residue is dissolved in 20% potassium carbonate and the solution extracted with ethyl acetate. The solvent is evaporated to obtain a reddish oil which is chromatographed in a column of activated magnesium silicate using benzene as the eluant. In this way there is obtained 5.2 g of a product in the form of a yellow oil, which is converted into the oxalate which is a crystalline product.

The oxalate is prepared in a solution in acetone. The acetone solution is diluted with diethyl ether and left to stand for 1 hour at −15° C. The oily precipitate is washed with diethyl ether and crystallisation started. The colourless crystals are washed with diethyl ether and recrystallised from acetone. The melting point of the oxalate is 112° C.

(2) The oxalate of the diethylaminoethyl ester of β-tetrahydrofuryl-β'-(3-biphenylyl)isobutyric acid By proceeding in the same way as described in the previous section using β-tetrahydrofuryl β'-(3-diphenylyl)-isobutyric acid as starting material, the product is obtained in the form of the oxalate, which has a melting point of 92° C.

(3) The oxalate of the diethylaminoethyl ester of β-tetrahydrofuryl-β'-(2-biphenylyl)isobutyric acid By proceeding in the same way as described in section (1) using β-tetrahydrofuryl β'-(2-biphenylyl)isobutyric acid as starting material, the product is prepared in the form of the oxalate, which has a melting point of 91°–93° C.

(4) The oxalate of the diethylaminoethyl ester of β-tetrahydrofuryl-β'-norbornyl isobutyric acid By proceeding in the same way as described in section (1) using β-tetrahydrofuryl β'-norbornyl isobutyric acid as starting material, the product is prepared in the form of the oxalate, which has a melting point of 71°–72° C.

(5) The oxalate of the diethylaminoethyl ester of β-tetrahydrofuryl-β'-(p-cyclohexylphenyl)isobutyric acid By proceeding in the same way as described in section (1) using β-tetrahydrofuryl β'-(p-cyclohexylphenyl) isobutyric acid as starting material, the product is prepared in the form of the oxalate, which has a melting point of 60° C.

The pharmacological activity of the new esters was established by means of the tests described below.

(1) Toxicity

Acute toxicity was determined in the mouse by the oral route. For all the compounds tested, the $LD_{50}$ was between 750 and 1100 mg/kg bodyweight.

(2) Antispasmodic Activity

This activity was determined on isolated rat intestine by the Magnus method. For determination of the inhibition of the contraction caused by barium chloride (musculotropic activity) the reference compound used was papaverine hydrochloride. The results obtained are expressed as the doses which inhibit 50% of the submaximal contraction induced by barium chloride. For determination of the inhibition of the contraction caused by acetyl choline (neurotropic activity) the reference compound used was atropine sulphate. The results obtained are expressed as the doses which inhibit 50% of the submaximal contraction obtained with atropine sulphate.

The results are set forth in the following table:

| Substance | Musculotropic activity g/ml | Neurotropic activity g/ml |
|---|---|---|
| Papaverine | $1.5 \times 10^{-6}$ | |
| Atropine | | $10^{-8}$ |
| The product of para. C-1 | $1.5 \times 10^{-6}$ | $10^{-6}$ |
| The product of para. C-2 | $3 \times 10^{-6}$ | $5 \times 10^{-6}$ |
| The product of para. C-3 | $3 \times 10^{-6}$ | $5 \times 10^{-6}$ |
| The product of para. C-4 | $5 \times 10^{-6}$ | $10^{-5}$ |
| The product of para. C-5 | $5 \times 10^{-6}$ | $10^{-5}$ |

The products tested all showed a spasmolytic effect of the same order as that of papaverine on spasms induced by barium chloride, while being distinctly less active than the action of atropine upon spasms induced by acetyl choline; this has the advantage that the side effects induced by a substance of the atropine type are avoided.

What is claimed is:

1. An ester having the formula

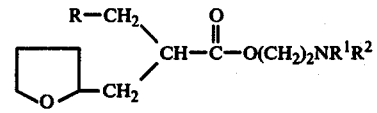

in which R is selected from the group consisting of biphenylyl, norbornyl and para-cyclohexyl phenyl, $R^1$ is a lower alkyl group and $R^2$ is a lower alkyl group, and salts thereof with pharmaceutically acceptable acids.

2. An ester as claimed in claim 1 in which each of $R^1$ and $R^2$ is an ethyl group.

3. The diethylaminoethyl ester of β-tetrahydrofuryl-β'-(4-biphenylyl)isobutyric acid and the acid oxalate thereof.

4. The diethylaminoethyl ester of β-tetrahydrofuryl-β'-(3-biphenylyl)isobutyric acid and the acid oxalate thereof.

5. The diethylaminoethyl ester of β-tetrahydrofuryl-β'-(2-biphenylyl)isobutyric acid and the acid oxalate thereof.

6. The diethylaminoethyl ester of β-tetrahydrofuryl-β'-norbornyl isobutyric acid and the acid oxalate thereof.

7. The diethylaminoethyl ester of β-tetrahydrofuryl-β'-(para-cyclohexylphenyl)isobutyric acid and the acid oxalate thereof.

8. A pharmaceutical composition which comprises (a) a pharmaceutically effective amount of an ester having the general formula

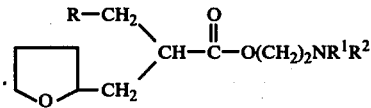

in which R is selected from the group consisting of biphenylyl, norbonyl and para-cyclohexylphenyl, $R^1$ is a lower alkyl group, and $R^2$ is a lower alkyl group, or a salt of said ester with a pharmaceutically acceptable salt, and (b) a pharmaceutically acceptable diluent.

9. The composition of claim 8 wherein said ester is the diethylaminoethyl ester of β-tetrahydrofuryl-β'-(4-biphenylyl)isobutyric acid.

* * * * *